United States Patent [19]

McCormick et al.

[11] Patent Number: 5,474,086
[45] Date of Patent: Dec. 12, 1995

[54] APPARATUS FOR MONITORING THE MOTION OF THE LUMBAR SPINE

[75] Inventors: Claude L. McCormick, Signal Mountain; Brian S. Baxter, Hixson, both of Tenn.; Brent E. Boxall, Lafayette, Ga.

[73] Assignee: Chattanooga Group, Inc., Hixson, Tenn.

[21] Appl. No.: 909,940

[22] Filed: Jul. 7, 1992

(Under 37 CFR 1.47)

[51] Int. Cl.$^6$ ............................................. A61B 5/103
[52] U.S. Cl. ............................................. 128/782
[58] Field of Search .................... 128/774, 782; 33/379; 272/134

[56] References Cited

U.S. PATENT DOCUMENTS

| | | | |
|---|---|---|---|
| 4,113,250 | 9/1978 | Davis | 272/93 |
| 4,462,252 | 7/1984 | Smidt et al. | 73/379 |
| 4,492,236 | 1/1985 | Pile | 128/781 |
| 4,565,368 | 1/1986 | Boettcher | 272/129 |
| 4,702,108 | 10/1987 | Amundsen et al. | 73/379 |
| 4,725,054 | 2/1988 | Solow et al. | 272/130 |
| 4,725,056 | 2/1988 | Rehrl et al. | 272/134 |
| 4,732,381 | 3/1988 | Skowronski | 272/134 |
| 4,768,779 | 9/1988 | Oehman et al. | 272/94 |
| 4,802,462 | 2/1989 | Reiss et al. | 272/134 |
| 4,805,455 | 2/1989 | DelGiorno et al. | 73/379 |
| 4,824,103 | 4/1989 | Smidt | 128/782 |
| 4,893,808 | 1/1990 | McIntyre et al. | 272/129 |
| 5,094,249 | 3/1992 | Marras et al. | 128/781 |

*Primary Examiner*—Max Hindenburg
*Attorney, Agent, or Firm*—Bell, Seltzer, Park & Gibson

[57] ABSTRACT

An apparatus is disclosed for monitoring the movement and force production of the lumbar spine during flexion and extension in each of several sagittal-frontal planes of the body, as well as during movement in the transverse (twisting) plane. The apparatus includes a rotatable platform upon which the patient is adapted to stand, and the platform is pivotable about a vertical axis, so that the platform may be pivoted to a selected angle and held in the selected position. For operation in the flexion/extension mode, there is provided a lever arm which is rotatable about a horizontal axis which is adapted to pass through the lumbro-sacral junction of the patient, and a first upper body engaging member is releasably mounted to the lever arm. A first computer controlled drive motor pivotally rotates the lever arm in opposite directions in accordance with a predetermined program. An overhead frame assembly is also mounted for rotation about the horizontal axis, and a second upper body engaging member is mounted to the overhead frame assembly for rotation about a generally vertical axis which is perpendicular to the horizontal axis. Thus the apparatus may be operated in a flexion/extension mode, or in a twisting mode, and with the foot platform in a selected angular position.

20 Claims, 9 Drawing Sheets

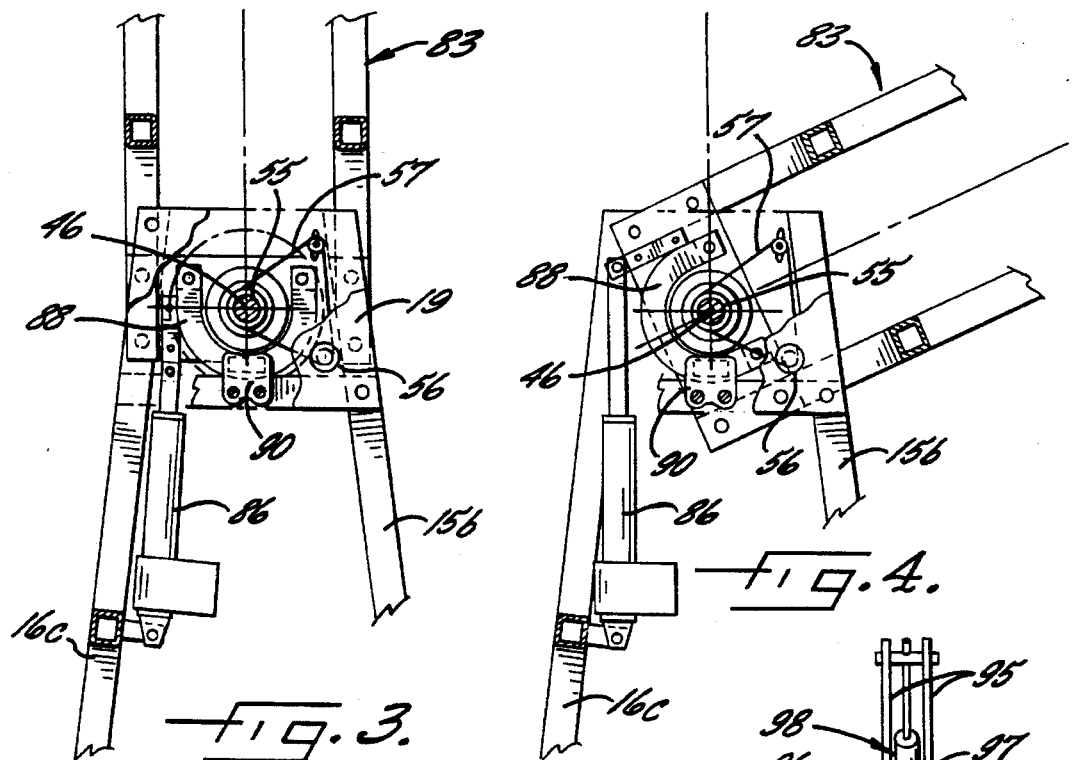
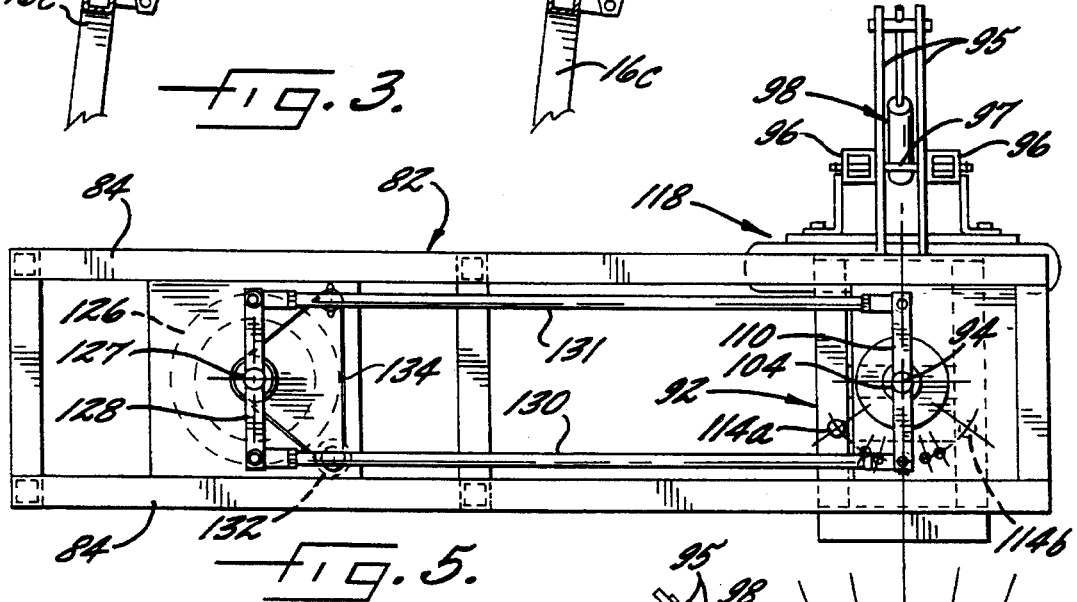
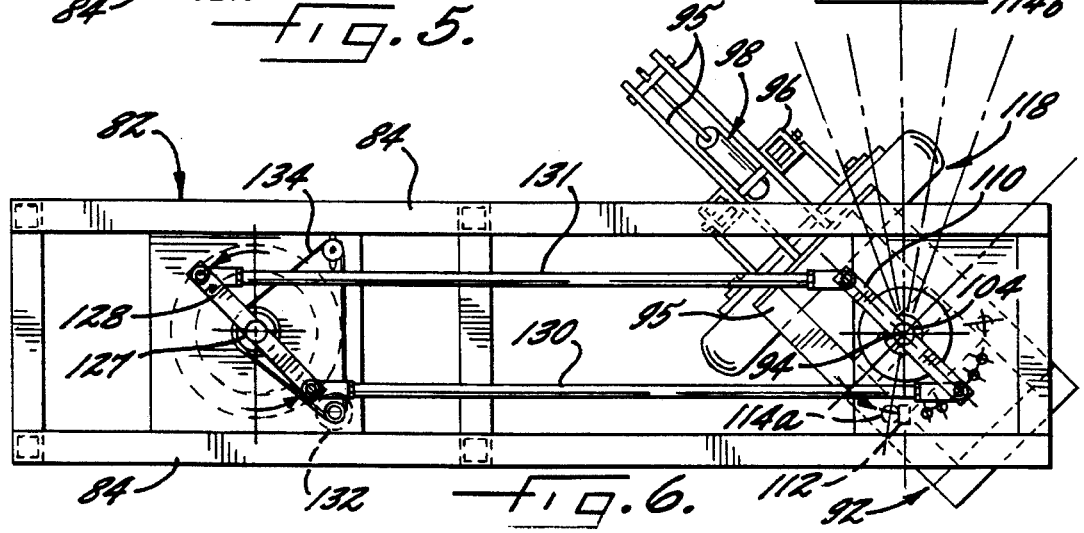

APPARATUS FOR MONITORING THE MOTION OF THE LUMBAR SPINE

BACKGROUND OF THE INVENTION

The present invention relates to an apparatus for monitoring the movement and force production of the lumbar spine during flexion and extension of the trunk of a patient in each of several sagittal-frontal planes of the body, and during trunk twisting. The apparatus is useful in the design of ergonomically suitable workplaces, and in the analysis and rehabilitation of low back disorders.

Occupationally related low back disorders have become a problem of epidemic proportion in the industrialized world in recent years, and has been recognized as a major problem in the industrial environment. It is widely known that the majority of low back disorders associated with the workplace involve muscular over-exertion injuries. These injuries occur frequently and are quite acute initially but may progress to a more chronic state with repetitive strains. One of the basic concepts in the ergonomic control of the workplace is to design manual materials handling tasks so that the strength required by the task does not exceed most workers capabilities.

Worker strength has traditionally been evaluated using isometric strength tests of workers in the sagittal plane, i.e. the extension/flexion plane. The machines which are currently marketed for measuring movement in the sagittal plane are of limited utility, however, since they can not assess motion components that are commonly found in the workplace or everyday life, and which are asymmetric. Machines of this general type are illustrated, for example, in Smidt et al, U.S. Pat. No. 4,462,252 and Boethcher, U.S. Pat. No. 4,565,368. Also, a similar machine is sold by Cybex, a division of Lumex, Inc. of Bay Shore, N.Y., and as described in U.S. Pat. No. 4,725,054 to Solow et al.

Machines are also available for assessing movement in the transverse (i.e. twisting) plane, and a machine of this general type is manufactured by Cybex, as the Cybex TR unit. Note also the Skowronski U.S. Pat. No. 4,732,381. Here again, however, these machines are of limited utility in that they are unable to assess commonly encountered motions which include components in addition to twisting.

Isotechnologies Inc., of Hillsboro, N.C., currently markets a low back testing and rehabilitation machine under the designation Iso Station® B-200, which includes a fixed platform upon which the patient stands, and a stabilizing belt system for locking the legs in a fixed upright position while the patient stands on the platform. The upper body is attached to a harness arrangement, which permits the upper body to move in three planes while the legs are fixed, namely the flexion/extension plane, the transverse (twisting) plane, and the lateral flexion plane. The apparatus also permits bending outside of the sagittal plane during flexion/extension movement. The movements in each of these planes are monitored, with the apparatus operated either dynamically or isometrically. This apparatus is also described in U.S. Pat. No. 4,768,779 to Oehman et al.

While the above described Iso Station® machine is better able to assess complex motion as compared to the above described single function machines, it does not permit the assessment of the lumbar movement of the spine in any specifically selected plane or combination of planes, since there is no control of the path of movement of the upper trunk. Thus there is an inherent inability to interpret the results accurately with respect to workplace determined demands, since patients produce different motions.

U.S. Pat. No. 5,094,249 to Marras et al discloses an apparatus for monitoring movement of the lumbar spine during flexion and extension, as well as during twisting. Also, the apparatus includes a platform upon which the patient stands and which is rotatable about a vertical axis, and so that the platform may be moved to and locked in a selected angular orientation, and the apparatus may then be operated in either a flexion/extension mode, or a twisting mode.

While the apparatus as described in the above patent to Marras represents a significant advance in the art in that it may be selectively configured to monitor the motion components during bending in the flexion/extension plane, or during movement in the transverse plane, and while assuming a symmetric or asymmetric trunk position, further improvement is deemed desirable in that the mass of the patient supporting framework is relatively large, which renders it difficult for the patient to easily start and stop the movements.

It is accordingly an object of the present invention to provide an apparatus which may be selectively configured to monitor the motion components during flexion/extension movement, or during twisting, and which has a moveable framework of reduced mass so as to provide easier control of the movements.

It is also an object of the present invention to provide an apparatus of the described type, and which is capable of operation in either mode while the patient assumes a symmetric or asymmetric trunk position.

SUMMARY OF THE INVENTION

The above and other objects and advantages of the present invention are achieved in the embodiment illustrated herein by the provision of an apparatus which comprises a main frame, and a horizontal platform which is adapted to support a patient in a standing position thereupon. A lever arm is mounted to the main frame for rotation about a horizontal axis which is positioned to pass approximately through the lumbro-sacral junction of a patient while the patient is standing upon the platform, and first upper body engaging member is mounted to the lever arm for engaging the upper body portion of a patient standing upon the platform and so that flexion and extension of the trunk of the patient causes the lever arm to pivot about the horizontal axis in at least one direction. A first dynamometer means is operatively connected to the lever arm for controlling the pivotal movement thereof in each pivotal direction.

An overhead frame assembly is mounted to the main frame for movement about the horizontal axis, and a second upper body engaging member is mounted to the overhead frame assembly for rotation about a twisting axis which is generally perpendicular to the horizontal axis and for engaging the upper body portion of a patient standing upon the platform. Also, a second dynamometer means is provided for controlling twisting movement of the second upper body member about the vertical axis.

In a preferred embodiment, the horizontal platform is mounted to the main frame for rotation about a vertical axis, and so that it can be rotated to and held in a selected rotational position. Also, an actuator is provided for pivoting the overhead frame assembly to a selected rotational position about the horizontal axis and holding the same in such position.

In use, the patient may perform flexion and extension of the trunk about the horizontal axis, with the first upper body engaging member contacting the body of the patient, and while the first dynamometer means controls the pivotal movement of the lever arm and thus the first upper body engaging member. Alternatively, the patient may perform twisting of the trunk about the twisting axis while the second upper body engaging member contacts the body of the patient, and while the second dynamometer means controls the twisting movement of the second upper body engaging member. Also, during flexion/extension movement, or during twisting movements, the trunk of the patient may be positioned in a symmetric or asymmetric position, by rotation of the platform to a selected rotational position. In addition, in the twisting mode, the overhead frame assembly may be pivoted to a selected rotational position about the horizontal axis so that the twisting movement may be performed while the patient is fully upright, or in a forwardly flexed position or a rearwardly extended position.

BRIEF DESCRIPTION OF THE DRAWINGS

Some of the objects and advantages of the present invention having been stated, others will appear as the description proceeds, when taken in conjunction with the accompanying drawings, in which

FIGS. 3 and 4 are fragmentary views taken substantially along the line 3—3 of FIG. 1, and illustrating the overhead frame assembly in the fully upright and forwardly inclined positions respectively;

FIGS. 5 and 6 are fragmentary plan views taken substantially along the line 5—5 of FIG. 1, and illustrating the twisting movement of the second upper body engaging member;

DETAILED DESCRIPTION OF THE PREFERRED EMBODIMENTS

Figure 1:
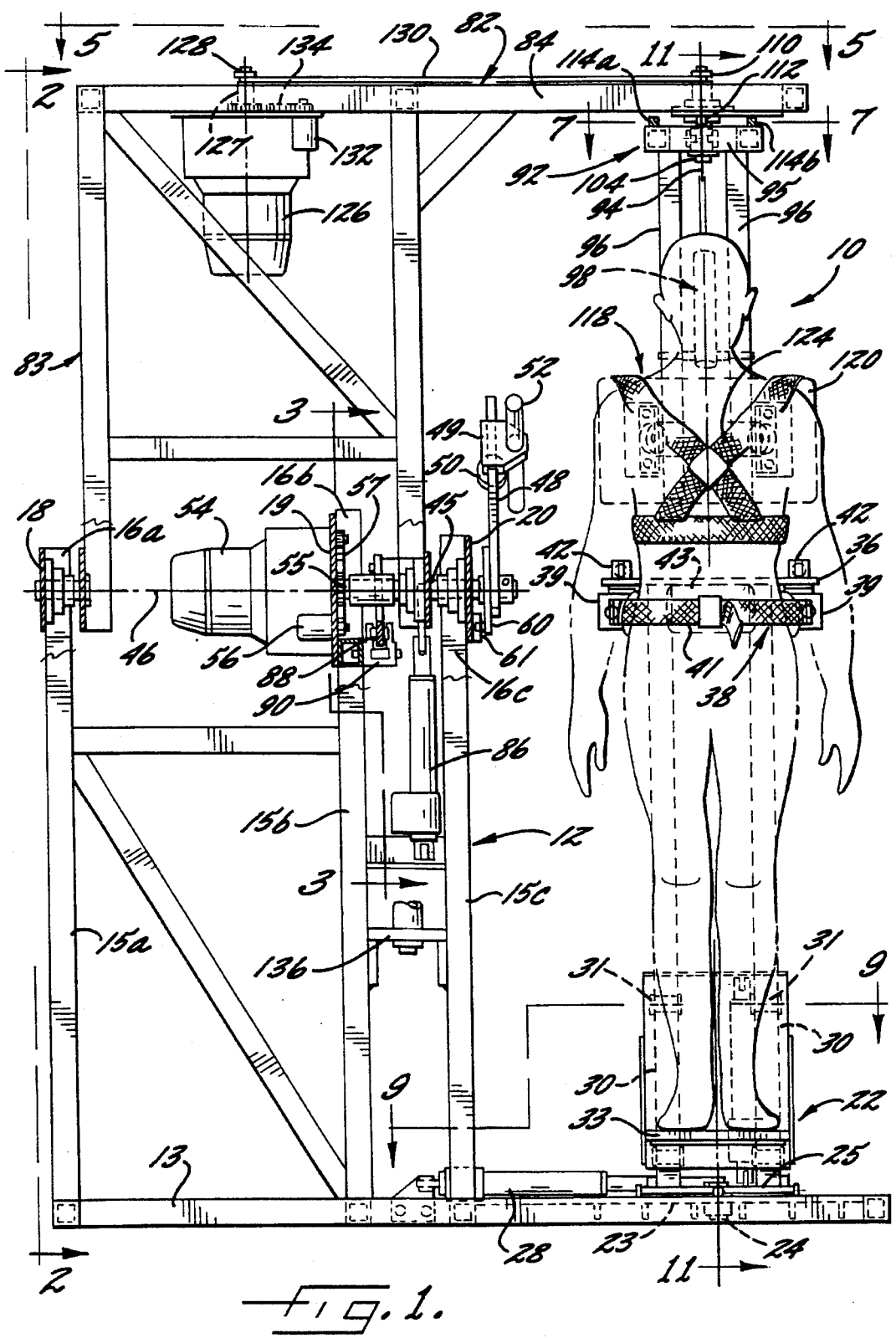
FIG. 1 is a front elevation view of an apparatus for monitoring the motion of the lumbar spine and which embodies the present invention, and with the apparatus configured for twisting movement of the patient.

Referring more particularly to the drawings, an apparatus which embodies the features of the present invention is indicated generally at 10. The overall apparatus 10 is best seen in FIG. 1, and it comprises a main frame 12, which is composed of a horizontal ground engaging rectangular base 13 and an upright framework which extends upwardly from the left side of the base 13 as seen in FIG. 1. The upright framework comprises a box-like arrangement of three front upright frame members 15a, 15b, 15c, and three rear upright frame members 16a, 16b and 16c. The upper ends of the frame members are horizontally interconnected by three vertically disposed plates 18, 19, and 20. The frame members are also laterally interconnected by other suitable frame members which are not specifically numbered.

Figure 9:
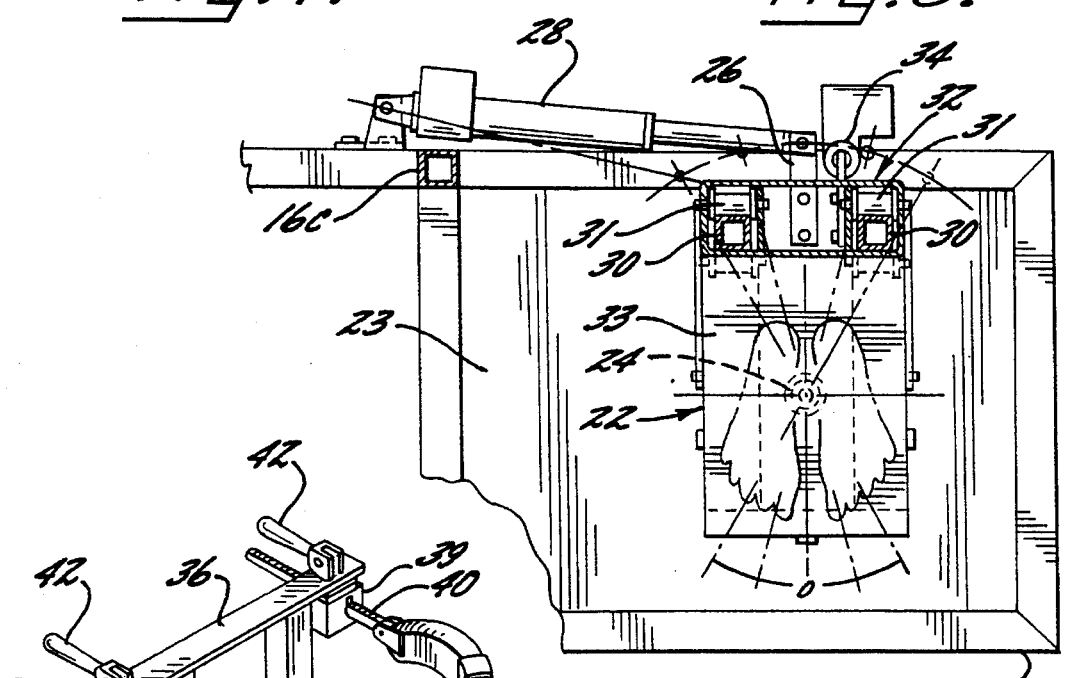
FIG. 9 is a fragmentary plan view of the base for the foot engaging platform of the apparatus, and taken substantially along the line 9—9 of FIG. 1.
Figure 11:
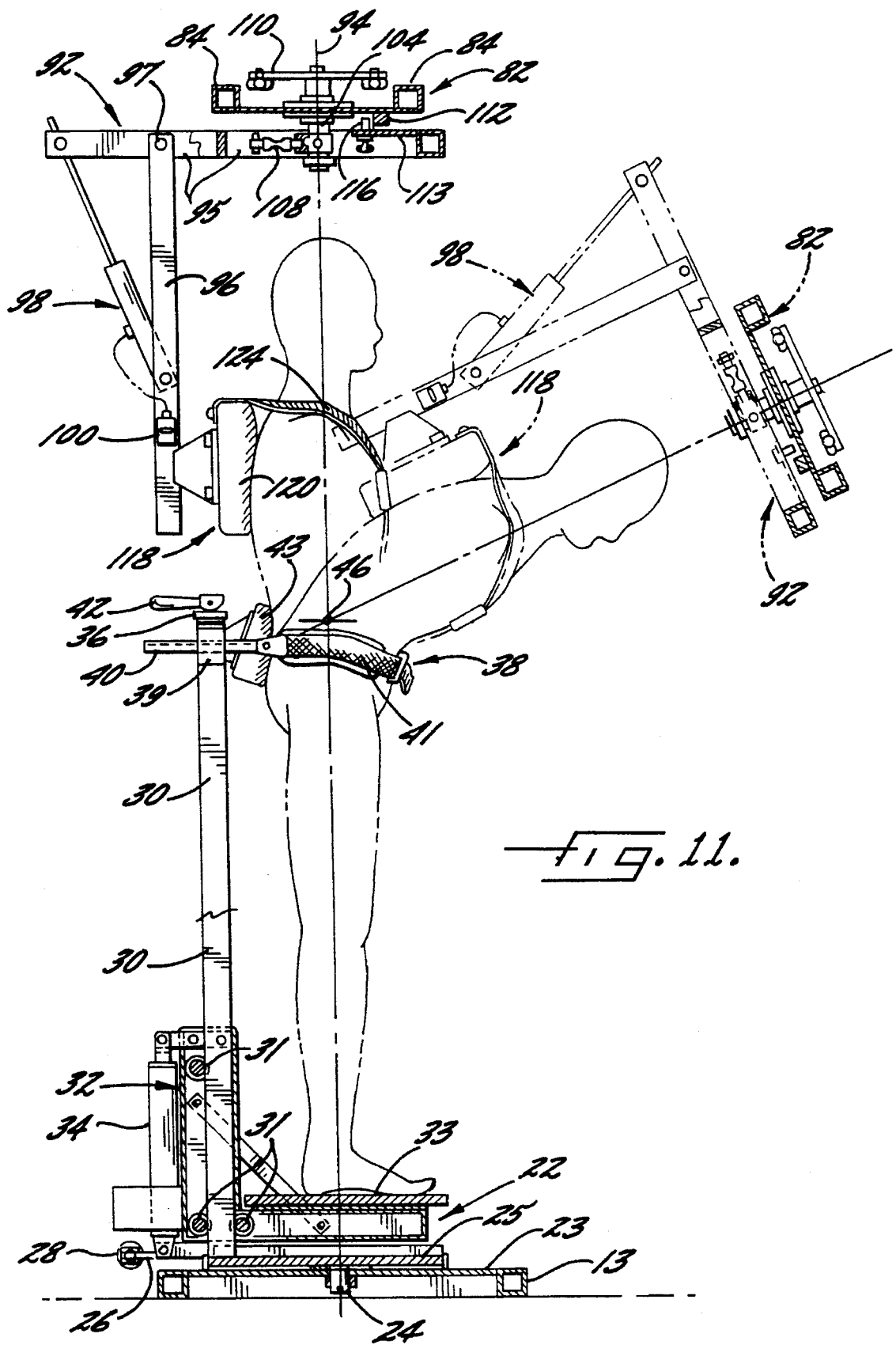
FIG. 11 is a side elevation view taken substantially along the line 11—11 of FIG. 1, and which is otherwise similar to FIG. 2.
Figure 12:
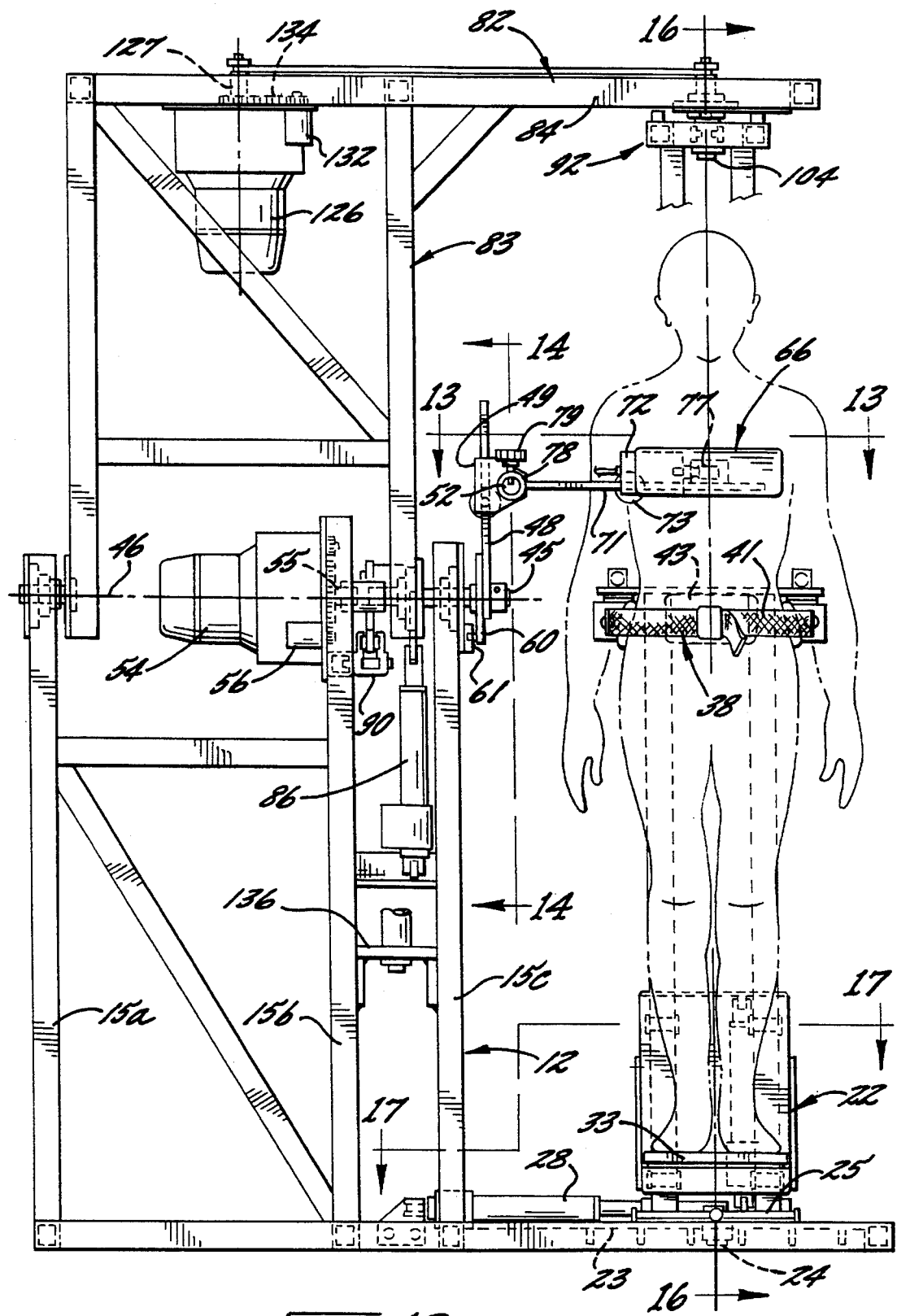
FIG. 12 is a view similar to FIG. 1, but with the apparatus configured for flexion/extension movement of the patient.

A platform assembly 22 is mounted to the right side of the base 13 of the main frame 12 as seen in FIG. 1, and the platform assembly 22 is mounted to a horizontal plate 23 which is fixed to the base 13, and as best seen in FIG. 11, the plate 23 mounts a vertical pivot pin 24. A bearing plate 25 is mounted immediately above the plate 23, and so as to permit rotation about the axis of the pivot pin 24. The rear edge of the bearing plate 25 mounts a bracket 26 (FIGS. 9 and 17–18) which is connected to an electric linear actuator 28, which may be operated to rotate the bearing plate 25 about the axis of the pin 24 and so that the bearing plate may be rotated to and locked in a selected rotational position.

The platform assembly 22 further includes a pair of vertical posts 30 which extend upwardly from the bearing plate 25. A support frame 32 having an L-shaped configuration in cross section (note FIGS. 9 and 11) is mounted for sliding movement along the vertical posts 30 by conventional roller bearings 31. The support frame 32 includes a horizontal platform 33, which is adapted to support a patient in a standing position thereupon, and the elevation of the frame and the platform on the posts is controlled by an electric linear actuator 34 so as to permit the apparatus to accommodate patients of varying height.

Figure 10:
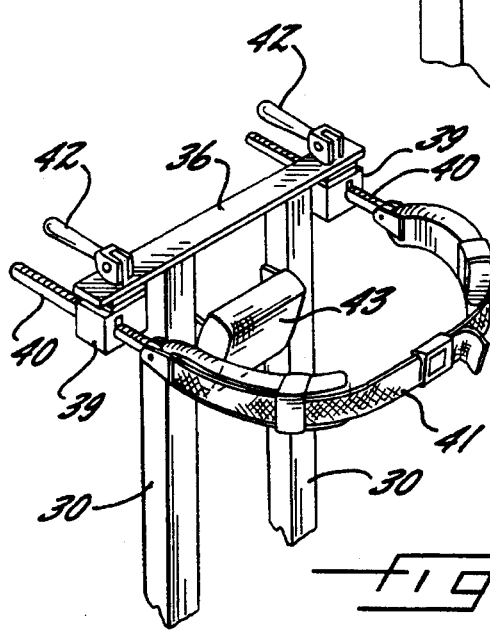
FIG. 10 is a perspective view of the pelvic stabilization assembly of the apparatus.

A cross bar 36 is mounted to the upper ends of the posts 30 and the cross bar 36 mounts a pelvic stabilizing assembly 38 as best seen in FIG. 10. A pair of blocks 39 are mounted at the ends of the cross bar 36, which in turn slidably receive two threaded rods 40 at the ends of a releasable waist band 41. The rods 40 are adapted to be locked in a selected position by the lever arms 42, in a conventional manner, and so that the waist band is adapted to firmly surround and support the pelvic region of the patient. The pelvic stabilization assembly 38 also includes a lower back pad 43 which is mounted between the posts 30, for engaging and supporting the lower back of the patient.

Figure 13:
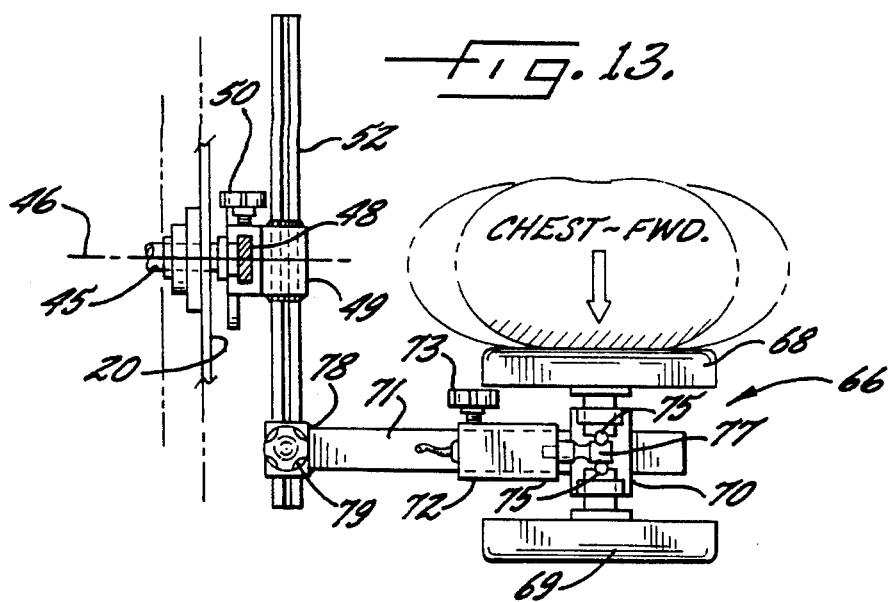
FIG. 13 is a fragmentary plan view of the first upper body engaging member and taken substantially along the line 13—13 of FIG. 12.

The main frame 12 rotatably mounts a drive shaft 45, which is mounted for rotation about a horizontal axis 46 which extends across and above the platform 33. As further described below, the axis 46 is positioned to pass approximately through the lumbro-sacral junction of a patient standing upon the platform. A radially directed lever arm 48 is mounted to one end of the drive shaft 45, and a slide 49 is mounted to the arm for slidable movement along the direction of the arm. Also, a threaded pin 50 (FIG. 13) is provided for locking the slide 49 at a selected elevation. The slide 49 in turn mounts a generally horizontal utility rod 52, which extends along a direction extending perpendicularly to the horizontal axis 46 and generally between the back and front of the patient standing upon the platform.

The apparatus 10 further includes a first dynamometer means which is mounted to the main frame 12 for controlling pivotal movement of the shaft 45 and lever arm 48 about the horizontal axis 46, in the manner described in more detail below. The dynamometer means includes a conventional permanent magnet reversible DC servo motor 54, which is operable at a variable speed, and which includes a built-in reduction gear box. A motor of this type is manufactured by PMI Motion Technologies of Commack, N.Y., as Model No. JR16M4CH.

The output shaft 55 of the motor 54 is coaxially connected to the drive shaft 45, and as best seen in FIGS. 1 and 3, the output shaft 55 is connected to a potentiometer 56 via a drive belt 57, which registers the rotational position of the shaft 55 and the motor 54.

Figures 14, 15:
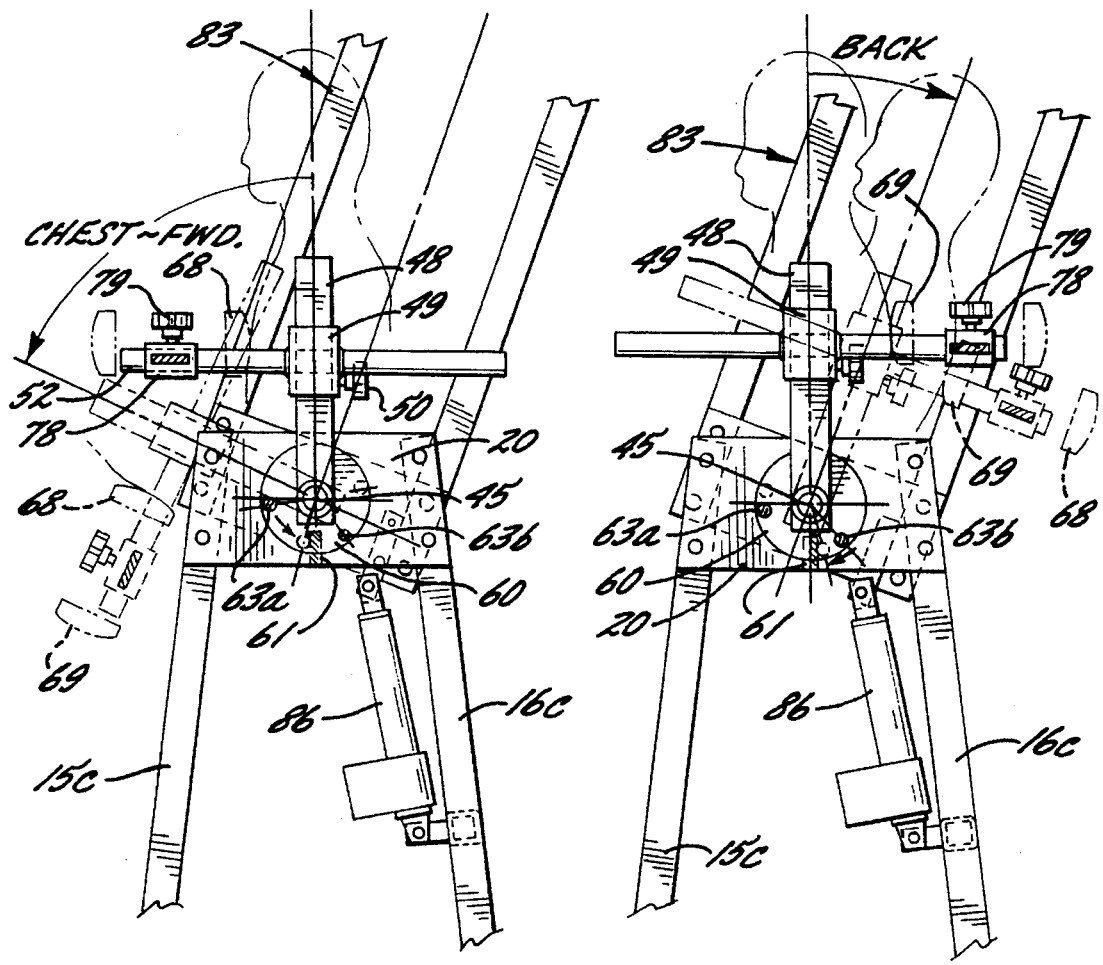
FIGS. 14 and 15 are fragmentary views taken substantially along the line 14—14 of FIG. 12, and illustrating the first upper body engaging member positioned to engage the chest and back of the patient respectively.

To physically limit the angular movement of the lever arm 48, a disc 60 is fixedly mounted to the shaft 45, so as to overlie the plate 20, note FIGS. 14 and 15. The plate 20 mounts a stop 61, and the disc 60 mounts a pair of pins 63a, 63b which contact the stop 61 to physically limit the rotation of the lever arm in each rotational direction from its upright position. As best seen in FIGS. 14 and 15, the pins 63a, 63b typically are positioned so that the lever arm 48 is able to rotate about 60° in the forward (flexion) direction from the upright position as shown by solid and phantom lines in FIG. 14, and about 20° in the rearward (extension) direction as shown by phantom lines in FIG. 15. The disc 60 may, if desired, also include openings (not shown) for receiving a removable pin, (not shown) which permits the rotational limits in each direction to be manually shortened.

A first body engaging member 66 is provided for use when the apparatus is configured for operation in the flexion/extension mode, and as illustrated in FIGS. 12–18. The first member 66 comprises a pair of elongate pads 68, 69 which are mounted for limited sliding movement on a cross arm 70. The cross arm 70 is slidably fixed to a support arm 71 by a sleeve 72 and locking pin 73, and each pad 68, 69 mounts a post 75 which is positioned to engage a load cell 77 (see FIG. 13) which indicates the force applied laterally between either one of the pads 68, 69 and the support arm 71. The support arm 71 includes a sleeve 78 and locking pin 79 at the remote end thereof for slidably mounting to the utility rod 52, and which also permits the member 66 to be removed from the utility rod 52. Thus when the patient is to undergo flexion (FIGS. 14 and 16), the member 66 is mounted to the forward end of the utility rod 52, and so that the elongate pad 68, engages the chest of the patient. When the patient is to undergo extension testing (FIG. 15 and 16), the member 66 is mounted to the rear end of the utility rod 52, and so that the elongate pad 69 engages the upper back of the patient.

The apparatus of the present invention also comprises an overhead frame assembly 82 (FIGS. 1 and 2) which includes a box-like framework 83 composed of several upright members and suitable interconnecting members which are not specifically numbered. The overhead frame assembly 82 also includes overhead beams 84 which extends horizontally from the upper end of the framework 83 to a position overlying the platform 33 upon which the patient stands (see also FIGS. 5–6).

The overhead frame assembly 82 is pivotally connected to the main frame 12 for movement about the horizontal axis 46, and an electrically operated linear actuator 86 is provided for pivoting the overhead frame assembly 82 to a selected rotational position about the horizontal axis 46 and holding the same in such position.

As best seen in FIGS. 3–4, a disc brake 88 is fixed to the overhead frame assembly 82 so as to partially surround the axis 46, and a conventional spring loaded brake caliper 90 is fixed to the frame 12 and engages the brake 88 so as to provide a controlled frictional resistance to the pivotal movement of the overhead frame assembly 82 at all times.

The apparatus of the present invention also includes a twist supporting frame 92 which is mounted to the overhead beams 84 of the frame assembly 82 for rotation about a twisting axis 94 which is generally perpendicular to the horizontal axis 46. As best seen in FIG. 11, the twist supporting frame 92 comprises a rectangular, generally horizontal upper segment 95, and a depending segment 96 which is pivotally connected to the upper segment 95 for pivotal movement about the axis of the pin 97. Also, a mechanical lock is provided which comprises a locking sleeve 98 mounted on a rod 99, and an actuator switch 100. A mechanical lock of this type is further disclosed in U.S. Pat. No. 3,874,480, and upon manual actuation of the switch 100, the sleeve 98 is able to slide relative to the rod 99. Thus the depending segment 96 is able to be selectively pivoted with respect to the upper segment 95 about the pivot pin 97.

Figure 7:
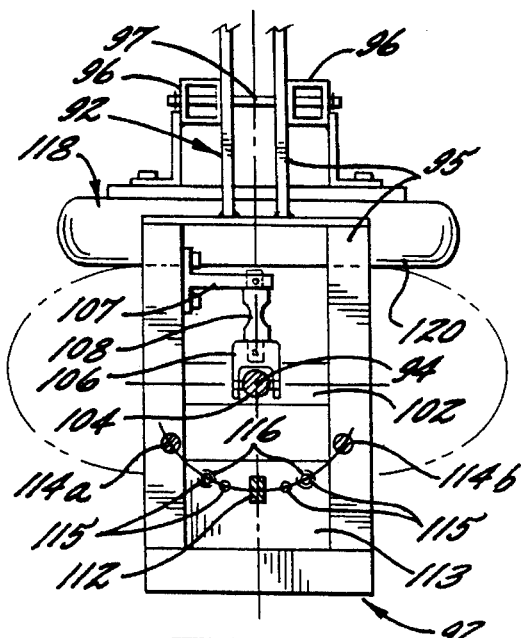
FIGS. 7 and 8 are fragmentary plan views taken substantially along the line 7—7 of FIG. 1 and further illustrating the twisting movement of the second upper body engaging member.
Figure 8:
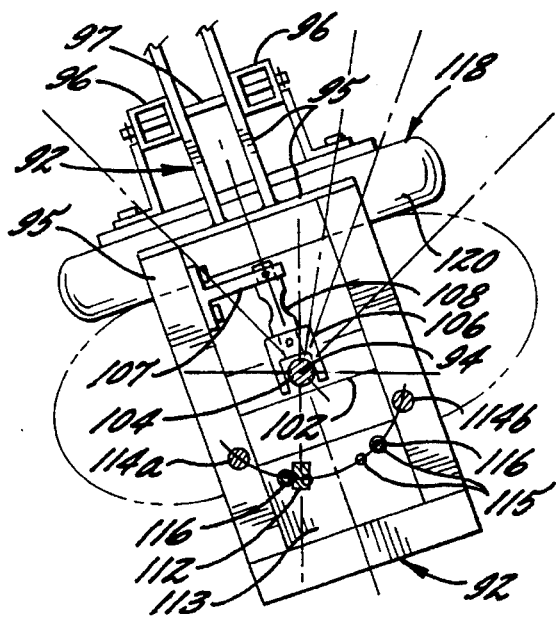

As best seen in FIGS. 7 and 8, the mounting structure for the twist supporting frame 92 comprises a cross arm 102 which is fixed to the horizontal upper segment 95, and a shaft 104 which extends perpendicularly through the cross arm 102, and which defines the twisting axis 94. The shaft 104 is rotatably mounted to the overhead beams 84 and to the cross arm 102 by means of suitable bearings, and the torque is transmitted from the shaft 104 to the twist supporting frame 92 via a transmission assembly (FIGS. 7 and 8) which includes a bracket 106 which is keyed to the shaft 104 so as to be locked against rotation with respect to the shaft 104. A second bracket 107 is fixed to the upper segment 95 of the twist supporting frame 92, and a load cell 108 is mounted between the two brackets 106, 107 so as to measure the torque imparted between the overhead beam and the twist supporting frame. Also, the upper end of the shaft 104 mounts a cross bar 110 (FIGS. 5–6), such that rotation of the cross bar causes a corresponding rotation of the twist supporting frame about the twisting axis 94.

Referring again to FIGS. 7–8 and 11, a stop 112 is fixed to the overhead frame 82, and a plate 113 is fixed to the twist supporting frame 92 below the stop. Also, the plate 113 includes a pair of pins 114a, 114b which are mounted along an arc centered at the shaft 104, and the pins 114a, 114b are each adapted to engage the stop 112 and thereby physically limit the twisting rotation of the twist supporting frame with respect to the overhead beam to about 45° in each direction (see for example FIG. 6). The plate 113 also includes pairs of openings 115 which are aligned on the same rotational arc, and which are each adapted to selectively receive removable pins 116 (FIGS. 7, 8 and 11) so as to physically engage the stop 112 and limit rotation at various angles of about 10° and 20° in one or both directions.

The second upper body engaging member 118 is mounted adjacent the lower end of the depending segment 96 of the twist supporting frame 92, and it comprises a back pad 120 which is mounted directly to the lower end portion of the depending segment. A chest harness 124 is fixed to the back pad 120, so that the upper body portion of the patient may be tightly held against the back pad 120 when the patient is standing upon the platform 33.

A second dynamometer means is provided for controlling twisting movement of the twist supporting frame 92 and thus the second upper body engaging member 118. More particularly, the second dynamometer means includes a second DC servo motor 126 which is mounted to the overhead frame assembly 82 and which may be identical to the motor 54. The motor 126 has an output shaft 127 which is parallel to the shaft 104, and a four bar linkage assembly (FIGS. 5 and 6) rotatably interconnects the output shaft 127 of the motor and the shaft 104. In the illustrated embodiment, the four bar linkage assembly comprises the cross bar 110 which is fixed to the shaft 104, and a cross bar 128 which is fixed to the output shaft 127 of the motor 126. Also, a pair of parallel tie rods 130, 131 interconnect the ends of the cross bars 110, 128. One of the tie rods 130, 131 is threadedly connected at each of its ends to the two cross bars, with the threads being oppositely directed in the nature of a turn-buckle, and so that rotation of the tie rod causes the cross bars 110, 128 to rotate in opposite directions and thereby permit any play in the linkage to be effectively eliminated. The second dynamometer means also includes a potentiometer 132 which is connected to the output shaft 127 of the motor 126 via a drive belt 134, so as to monitor the rotational position of the shaft and motor.

Figure 2:
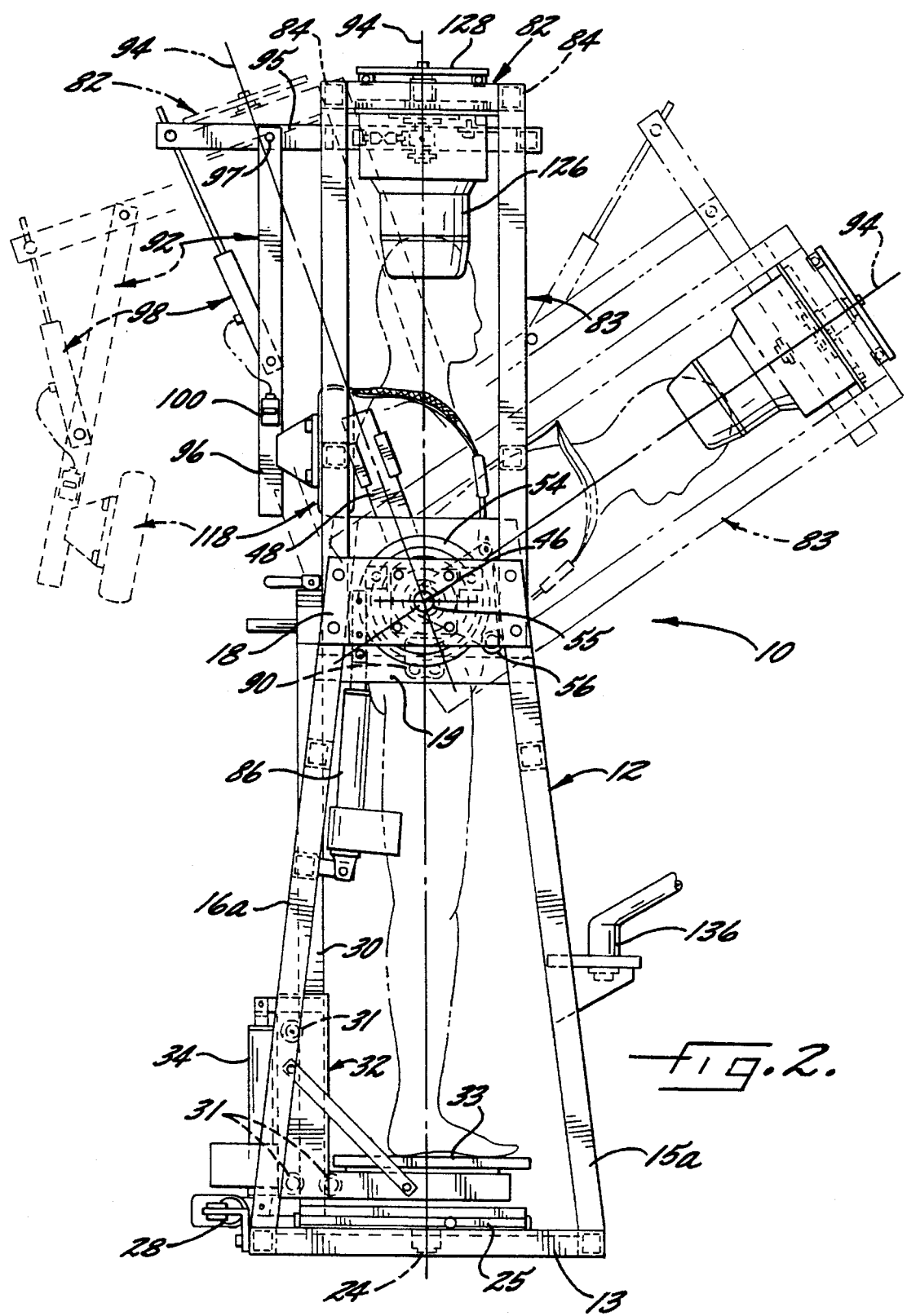
FIG. 2 is a side elevation view of the apparatus taken substantially along the line 2—2 of FIG. 1, with the apparatus being shown in the fully upright position in solid lines, and in the forwardly and rearwardly inclined positions in broken lines.

The two dynamometer means of the present invention include a computer control system, which includes a predetermined program for monitoring the output signals from the two load cells 77, 108 and potentiometers 56, 132, and for controlling the operation of the drive motors 54, 126 in accordance with the program. In this regard, the program may be designed for testing under isokinetic, isotonic, isometric conditions, or any other protocol. Also, in accordance with conventional technology, protocols may be employed which require the patient to perform an interactive task by monitoring a computer screen (not shown) of the computer that controls and records the action of the drive motors. In this regard, a computer terminal (not shown) may be conveniently positioned on a stand which is pivotally mounted to the main frame of the apparatus at 136 as seen in FIG. 2, and so as to pivot about a vertical axis and be movable to a position in front of the patient and thus readily visible.

Flexion/Extension Operation

Figure 16:
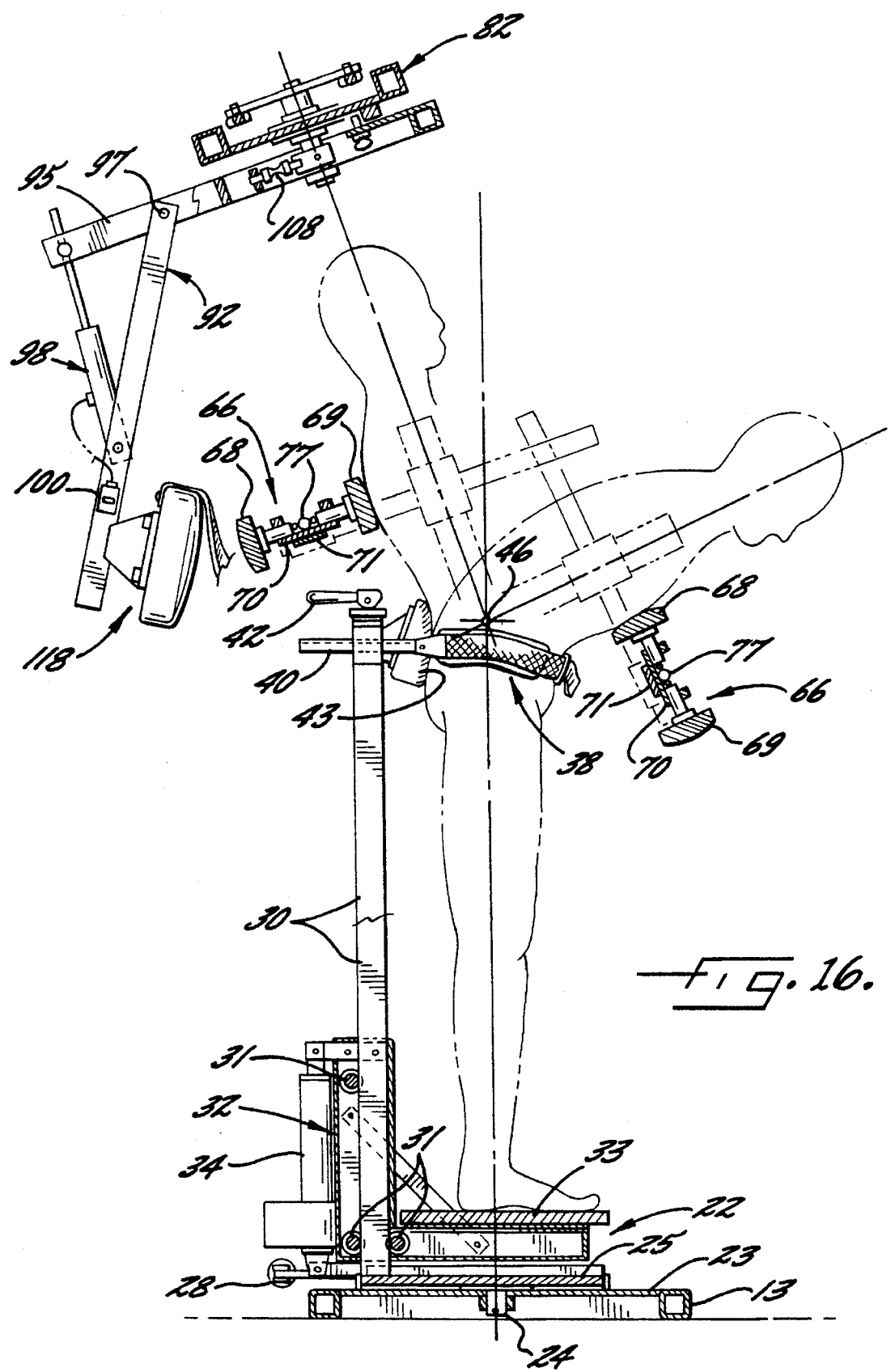
FIG. 16 is a fragmentary view taken substantially along the line 16—16 of FIG. 12 and illustrating the position of the overhead frame assembly during operation in the flexion/extension mode.

When the apparatus 10 is to be operated in the flexion/extension mode as seen in FIGS. 12–18, the overhead frame assembly 82 is pivoted to a rearward position as seen in FIG. 16, by the actuator 86. Also, the twist supporting frame 92 is pivoted about the axis of the pin 97 to its withdrawn position.

The patient is then positioned to stand upon the platform 33, and the elevation thereof is adjusted by the operation of the linear actuator 34 until the juncture between the fixed vertebrae and moveable vertebrae of the spine (i.e. the lumbro-sacral junction at L5-S1) is approximately aligned with the horizontal axis 46. The pelvic stabilization assembly 38 is then attached to the pelvic region of the patient. Next, the upper body engaging member 66 is mounted to either the front or rear end of the utility rod 52. More particularly, where flexion is to be monitored, the member 66 is mounted to the forward end of the rod and so that the pad 68 engages the chest of the patient, note FIG. 14. The elevation of the member 66 with respect to the chest may be adjusted by sliding the slide 49 along the lever arm 48. Where extension is to be monitored, the member 66 is mounted to the rear end of the rod 52, note FIG. 15, and so that the pad 69 engages the upper back of the patient at the selected elevation.

Before initiating operation, the maximum flexion and extension angles are recorded in the computer control system by signals from the potentiometer, i.e. the lever arm 48 is moved to the desired angles and the signals are electronically recorded. In this regard, the maximum range of movement is mechanically limited by the stop 61 and pins 63a, 63b, which serve as a safety back-up in the event of a computer control system failure. Where additional openings are provided in the disc 60 as described above, the maximum range of movement may be shortened by the insertion of pins in such openings.

The apparatus 10 is then ready to be set into operation in accordance with the operating program provided by the computer control system. While in operation, the load cell 77 of the body engaging member 66 interfaces with the patient, and its output signal is fed to the computer control, along with a signal from the potentiometer 56, which is indicative of the angular position of the drive motor 54 and the lever arm 48.

Figure 17:
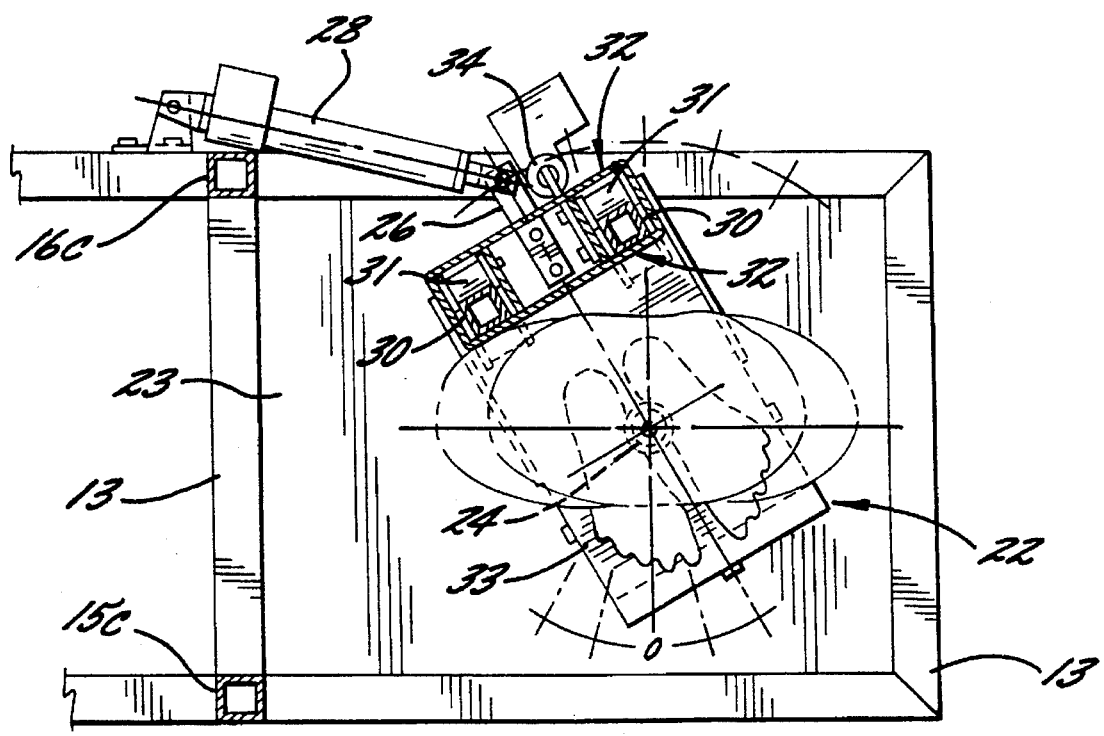
FIGS. 17–18 are views similar to FIG. 9, but illustrating the foot platform rotated and locked in the maximum left hand and right hand positions respectively.
Figure 18:
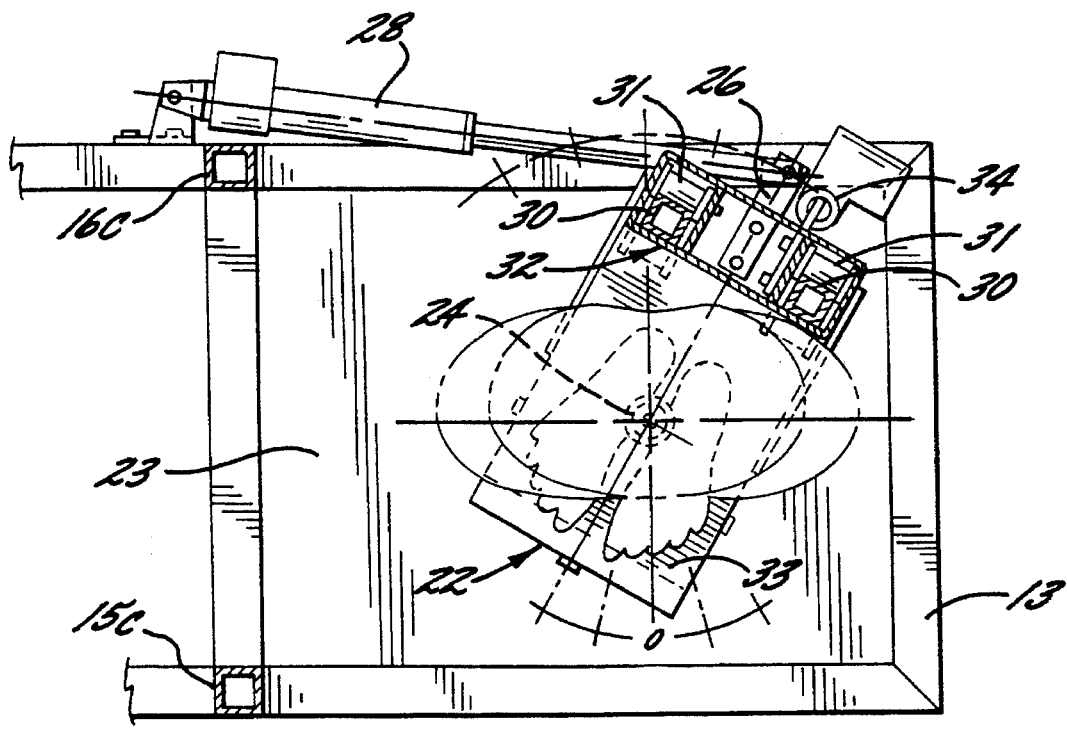

In order to operate in planes outside of the sagittal plane, the platform 33 is rotated and locked into a predetermined angular orientation by operation of the actuator 28 and as illustrated in FIGS. 17 and 18.

Twisting Operation

In the twisting mode (FIGS. 1–11), the upper body engaging member 66 is removed from the rod 52. Then the patient is positioned to stand upon the platform 33, and the pelvic region is stabilized by means of the pelvic stabilization assembly 38 in the manner described above. In addition, the twist supporting frame 92 is pivoted forwardly about the pin 97 to its operative position as best seen in FIG. 11, and so that the back pad 120 of the upper body engaging member 118 rests against the back of the patient. The harness 124 is then engaged across the chest of the patient, so that the upper body is firmly pressed against the pad 120 by the harness 124. Also, the patient is preferably positioned so that the twisting axis 94 is aligned along the lumbro-sacral axis of the patient.

The overhead frame assembly 82 is typically positioned in its fully upright position, although the frame assembly may if desired be inclined in either direction from the fully upright position by operation of the actuator 86, note FIG. 2. The engagement between the spring loaded brake caliper 90 and the brake 88 provides sufficient friction to provide smooth operation. Brake shoe 88 is also engaged, to firmly lock the overhead frame assembly 82 in its fully upright, or other selected operating orientation.

Before initiating the operation, the twist angle in each direction is electronically recorded by rotating the twist supporting frame to the desired positions and recording the signals from the potentiometer 132. Also it will be understood that the maximum twist in each direction is mechanically limited by the stop 112 and pins 114a, 114b, and that this range of movement may be shortened by the insertion of pins in the openings 115. During operation, the load cell 108 measures the force the patient applies to the twist supporting frame 92, or the force being applied to the patient, depending upon the programmed protocol. Also, the potentiometer 132 reads the angular position of the drive motor 126, as well as the twisting angle of the twist supporting frame 92 with respect to the overhead frame assembly 82, and the signals from the load cell 108 and the potentiometer 132 are fed to the computer control system.

In the drawings and specification, there has been set forth a preferred embodiment of the invention, and although specific terms are employed, they are used in a generic and descriptive sense only and not for purposes of limitation.

That which is claimed is:

1. An apparatus for monitoring the movement of the lumbar spine during flexion and extension of the trunk of a patient, and during trunk twisting, and comprising a main frame, a horizontal platform mounted to said main frame and being adapted to support a patient in a standing position thereupon, a lever arm, means mounting said lever arm to said main frame for rotation about a horizontal axis with said lever arm extending generally radially therefrom, and with said horizontal axis being positioned to pass approximately through the lumbro-sacral junction of a patient while the patient is standing upon said platform, a first upper body engaging member mounted to said lever arm for engaging the upper body portion of a patient standing upon said platform and so that flexion and extension of the trunk of the patient causes said lever arm to pivot about said horizontal axis in at least one direction, first dynamometer means comprising a reversible first drive motor operatively connected to said lever arm for controlling the pivotal movement thereof in each pivotal direction, an overhead frame assembly, means mounting said overhead frame assembly to said main frame for pivotal movement about said horizontal axis, a second upper body engaging member, means mounting said second upper body engaging member to said overhead frame assembly for rotation about a twisting axis which is generally perpendicular to said horizontal axis and for engaging the upper body portion of a patient standing upon said platform and such that twisting of the trunk of the patient causes said second upper body engaging member to twist about said twisting axis, and second dynamometer means including a reversible second drive motor for controlling twisting movement of said second upper body engaging member about said twisting axis, whereby the patient may selectively perform flexion and extension of the trunk about said horizontal axis while said first dynamometer means controls the pivotal movement of said lever arm, or perform twisting of the trunk and while said second dynamometer means controls the twisting movement of said second upper body engaging member.

2. The apparatus as defined in claim 1 wherein said reversible first drive motor is mounted to said main frame for controlling rotation of said lever arm about said horizontal axis, and said reversible second drive motor is mounted to said overhead frame assembly for controlling rotation of said second upper body engaging member about said twisting axis.

3. The apparatus as defined in claim 2 further comprising actuator means for pivoting said overhead frame assembly to a selected rotational position about said horizontal axis and holding the same in such position, and such that the patient can perform a twisting movement while positioned in a fully upright position or in a forwardly flexed or rearwardly extended position.

4. The apparatus as defined in claim 3 wherein said horizontal platform is mounted to said main frame for rotation about a vertical axis, and said apparatus further comprises means for locking said platform to said main frame in a selected rotational position with respect to said main frame.

5. The apparatus as defined in claim 4 wherein said locking means comprises second actuator means for selectively rotating said platform to a selected rotational position and holding the same in such position.

6. The apparatus as defined in claim 4 further comprising pelvic stabilization means for releasable connection to the pelvic region of the trunk of a patient standing upon said platform so as to support the pelvic region of the trunk in a fixed position with respect to said main frame.

7. The apparatus as defined in claim 6 further comprising means mounting said platform to said main frame so as to permit vertical adjustment of the height thereof, whereby the apparatus may be configured to accommodate patients of varying height.

8. The apparatus as defined in claim 1 wherein said first upper body engaging member comprises an elongate pad assembly, and means for releasably mounting said pad assembly to said lever arm at an adjustable location along a line extending perpendicular to said horizontal axis and generally between the back and front of the patient standing upon said platform, and whereby said pad assembly may be positioned to engage either the chest or the upper back of the patient.

9. The apparatus as defined in claim 1 wherein said means mounting said second upper body engaging member to said overhead frame assembly comprises a twist supporting frame which is mounted to said overhead frame assembly for rotation about said twisting axis, and said second upper body engaging member comprises a back pad and a chest harness which are mounted to said twist supporting frame.

10. The apparatus as defined in claim 9 wherein said twist supporting frame comprises an upper segment which is rotatably connected to said overhead frame assembly, and a depending segment which is connected to said upper segment and which mounts said back pad and chest harness.

11. The apparatus as defined in claim 10 further comprising means to physically limit the rotation of said lever arm about said horizontal axis to a selected angular rotation in each direction, and means to physically limit the rotation of said twist supporting frame about said twisting axis to a selected angular rotation in each direction.

12. The apparatus as defined in claim 11 wherein said depending segment of said twist supporting frame is pivotally mounted to said upper segment thereof for pivotal movement about a generally horizontal pivot axis, and further comprising means for locking the depending segment in a selected pivotal position about said pivot axis and so that said back pad and chest harness may be moved to a withdrawn position during operation in the flexion/extension mode.

13. The apparatus as defined in claim 2 wherein said first dynamometer means further comprises first force transducer means for measuring the force applied between said first upper body engaging member and the patient, first rotation sensing means for monitoring the angular position of said lever arm, and computer control means including a predetermined program for monitoring the output signals from said first force transducer means and said first rotation sensing means, and for controlling the operation of said first drive motor in accordance with said program.

14. The apparatus as defined in claim 13 wherein said second dynamometer means further comprises second force transducer means for measuring the twisting force applied between said second upper body engaging member and the patient, second rotation sensing means for monitoring the angular position of said twist supporting frame with respect to said overhead frame assembly about said twisting axis, and wherein said computer control means further includes a predetermined program for monitoring the output signals from said second force transducer means and said second rotation sensing means, and for controlling the operation of said second drive motor in accordance with said program.

15. The apparatus as defined in claim 14 wherein said second drive motor includes an output shaft which is parallel to and spaced from said twisting axis, and further comprising transmission means for rotatably interconnecting said output shaft and said twist supporting frame.

16. The apparatus as defined in claim 15 wherein said transmission means comprises a drive shaft fixedly connected to said second upper segment of said twist supporting frame and rotatably connected to said overhead frame assembly for rotation about said twisting axis, a pair of cross bars fixedly mounted to said output shaft and said drive shaft respectively, and a pair of tie rods interconnecting respective opposite ends of said cross bars so as to form a four bar linkage, with at least one of said tie rods being threadedly connected to the pair of cross bars with oppositely directed threads so as to form a turnbuckle which permits elimination of play between the two cross bars.

17. An apparatus for monitoring the movement of the lumbar spine during flexion and extension of the trunk of a patient, and during trunk twisting, and comprising a main frame, a horizontal platform adapted to support a patient in standing position thereupon, means mounting said platform to said main frame for rotation about a vertical axis and for locking said platform in a selected rotational position, a lever arm, means mounting said lever arm to said main frame for rotation about a horizontal axis with said lever arm extending generally radially therefrom, and with said horizontal axis being positioned to pass approximately through the lumbro-sacral junction of a patient while the patient is standing upon said platform a first upper body engaging member mounted to said lever arm for engaging the upper body portion of a patient standing upon said platform and so that flexion and extension of the trunk of the patient causes said lever arm to pivot about said horizontal axis in at least one direction, first dynamometer means including a first drive motor which is operatively connected to said lever arm for controlling the pivotal movement thereof in each pivotal direction, a twist supporting frame mounted to said main frame for rotation about a twisting axis which is generally perpendicular to said horizontal axis, a second upper body engaging member mounted to said twist supporting frame for engaging the upper body portion of a patient standing upon said platform and such that twisting of the trunk of the patient causes said second upper body engaging member and said twist supporting frame to twist about said twisting axis, and second dynamometer means including a second drive motor which is operatively connected to said twist supporting frame for controlling twisting movement of said second upper body engaging member and said twist supporting frame about said twisting axis, an overhead frame assembly pivotally mounted to said main frame for pivotal movement about Said horizontal axis, and including a horizontal beam which extends above said platform, and with said twist supporting frame being pivotally mounted to said beam for rotation about said twisting axis, and actuator means for moving said overhead frame assembly to a selected rotational position and locking the same in such position, whereby the patient may selectively perform flexion and extension of the trunk about said horizontal axis while said first dynamometer means controls the pivotal movement of said lever arm, or perform twisting of the trunk and while said second dynamometer means controls the twisting movement of said second upper body engaging member.

18. The apparatus as defined in claim 17 wherein said twist supporting frame comprises an upper segment which is rotatably connected to said overhead beam, and a depending segment, and wherein said second upper body engaging member is mounted to said depending segment.

19. The apparatus as defined in claim 18 wherein said depending segment is pivotally mounted to said upper segment so as to permit pivotal movement about a generally horizontal pivot axis, and further comprising means for locking the depending segment and the upper segment in a selected pivotal position about said pivot axis and so that said second upper body engaging member may be moved to a withdrawn position during operation in the flexion/extension mode.

20. The apparatus as defined in claim 19 wherein said first upper body engaging member is releasably mounted to said lever arm so as to permit removal of said first upper body engaging member during operation in the twisting mode.

* * * * *